(12) United States Patent
Haibach

(10) Patent No.: US 9,364,632 B2
(45) Date of Patent: Jun. 14, 2016

(54) MANUALLY ACTUATED TALK VALVE FOR A RESPIRATORY DEVICE

(75) Inventor: Richard Thomas Haibach, Murrysville, PA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 381 days.

(21) Appl. No.: 13/813,984

(22) PCT Filed: Aug. 17, 2011

(86) PCT No.: PCT/IB2011/053627
§ 371 (c)(1),
(2), (4) Date: Feb. 4, 2013

(87) PCT Pub. No.: WO2012/023107
PCT Pub. Date: Feb. 23, 2012

(65) Prior Publication Data
US 2013/0139820 A1   Jun. 6, 2013

Related U.S. Application Data

(60) Provisional application No. 61/375,110, filed on Aug. 19, 2010.

(51) Int. Cl.
*A61M 16/06* (2006.01)
*A61M 16/08* (2006.01)
*A61M 16/20* (2006.01)
*A61M 16/00* (2006.01)
*A61M 16/04* (2006.01)

(52) U.S. Cl.
CPC ....... *A61M 16/0666* (2013.01); *A61M 16/0066* (2013.01); *A61M 16/04* (2013.01); *A61M 16/06* (2013.01); *A61M 16/0875* (2013.01); *A61M 16/20* (2013.01); *A61M 16/208* (2013.01)

(58) Field of Classification Search
CPC ..... A61F 2/20; A61M 16/00; A61M 16/0066; A61M 16/04; A61M 16/0463; A61M 16/06; A61M 16/0666; A61M 16/08; A61M 16/0816; A61M 16/0875; A61M 16/20; A61M 16/202; A61M 16/208; A62B 18/08
USPC ............. 128/201.19, 202.27, 205.24, 207.14, 128/207.15, 207.16, 207.18, 912; 623/9
See application file for complete search history.

(56) References Cited

U.S. PATENT DOCUMENTS 4,592,349 A   6/1986 Bird
4,593,689 A * 6/1986 White ...................... 128/201.19
(Continued)

FOREIGN PATENT DOCUMENTS

CN   2054696 U    3/1990
CN   200977321 Y  11/2007
(Continued)

*Primary Examiner* — Annette Dixon
(74) *Attorney, Agent, or Firm* — Michael W. Haas

(57) ABSTRACT

An interface system for use in providing a flow of pressurized gas to a patient. The interface system comprises a mask (18) structured to engage a nasal and/or oral orifice of a patient, a conduit (16) coupled to the mask, and a valve mechanism (20) operatively coupled to the mask or the conduit. The conduit is structured to communicate the flow of pressurized gas to the mask. The valve mechanism is structured to selectively impede the flow of pressurized gas to the patient and is actuated by the patient, thus allowing the patient to speak without interference from the flow of pressurized gas.

6 Claims, 5 Drawing Sheets

(56) References Cited

U.S. PATENT DOCUMENTS

| | | | |
|---|---|---|---|
| 4,633,864 A * | 1/1987 | Walsh | 128/207.15 |
| 4,718,415 A | 1/1988 | Bolnberger | |
| 4,774,945 A * | 10/1988 | White et al. | 128/207.18 |
| 4,869,244 A | 9/1989 | Nentchev | |
| 5,411,021 A | 5/1995 | Gdulla | |
| 5,495,848 A | 3/1996 | Aylsworth | |
| 5,720,282 A * | 2/1998 | Wright | A61M 16/04 128/203.12 |
| 6,016,802 A | 1/2000 | Jackson | |
| 6,206,003 B1 | 3/2001 | Burch | |
| 6,920,880 B1 | 7/2005 | Zahrt | |
| 7,296,568 B2 | 11/2007 | Capon | |
| 7,458,390 B2 | 12/2008 | Gossweiler | |
| 2009/0266364 A1 | 10/2009 | Nysaether | |
| 2012/0055471 A1 * | 3/2012 | Hadas et al. | 128/201.19 |

FOREIGN PATENT DOCUMENTS

| | | |
|---|---|---|
| EP | 0566400 B1 | 3/1997 |
| EP | 0771577 A1 | 6/1997 |
| GB | 2459305 A | 10/2009 |
| JP | S52146092 A | 12/1977 |
| JP | S63135952 A | 6/1988 |
| WO | 8202147 A1 | 7/1982 |
| WO | 9616688 A1 | 6/1996 |
| WO | WO02092170 A2 | 11/2002 |

\* cited by examiner

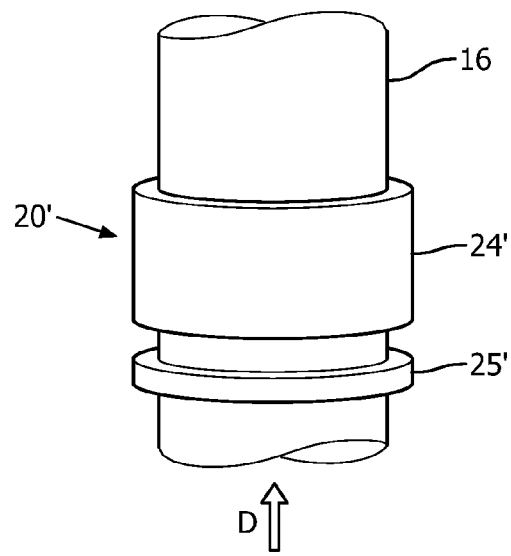
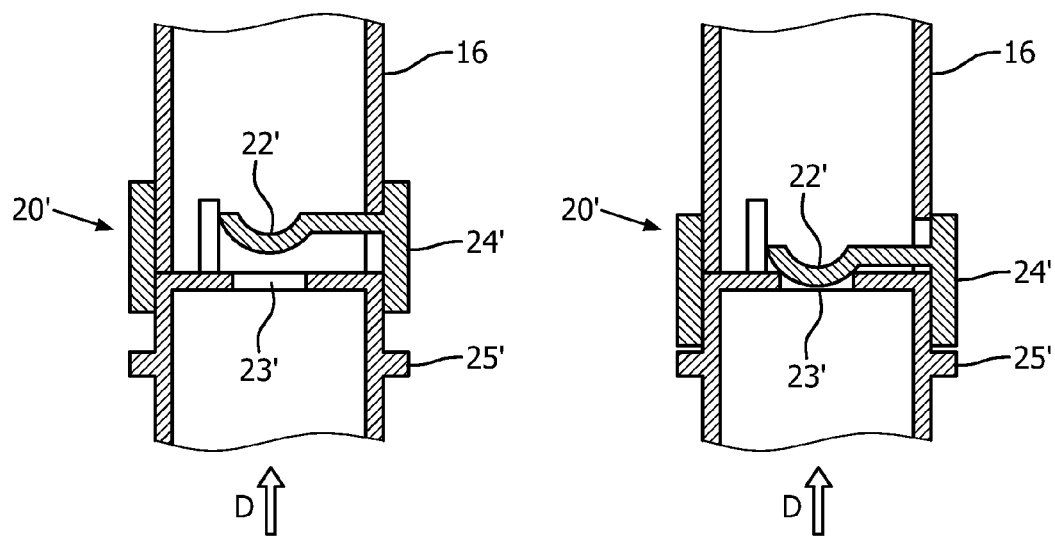
FIG. 4
FIG. 5  FIG. 6

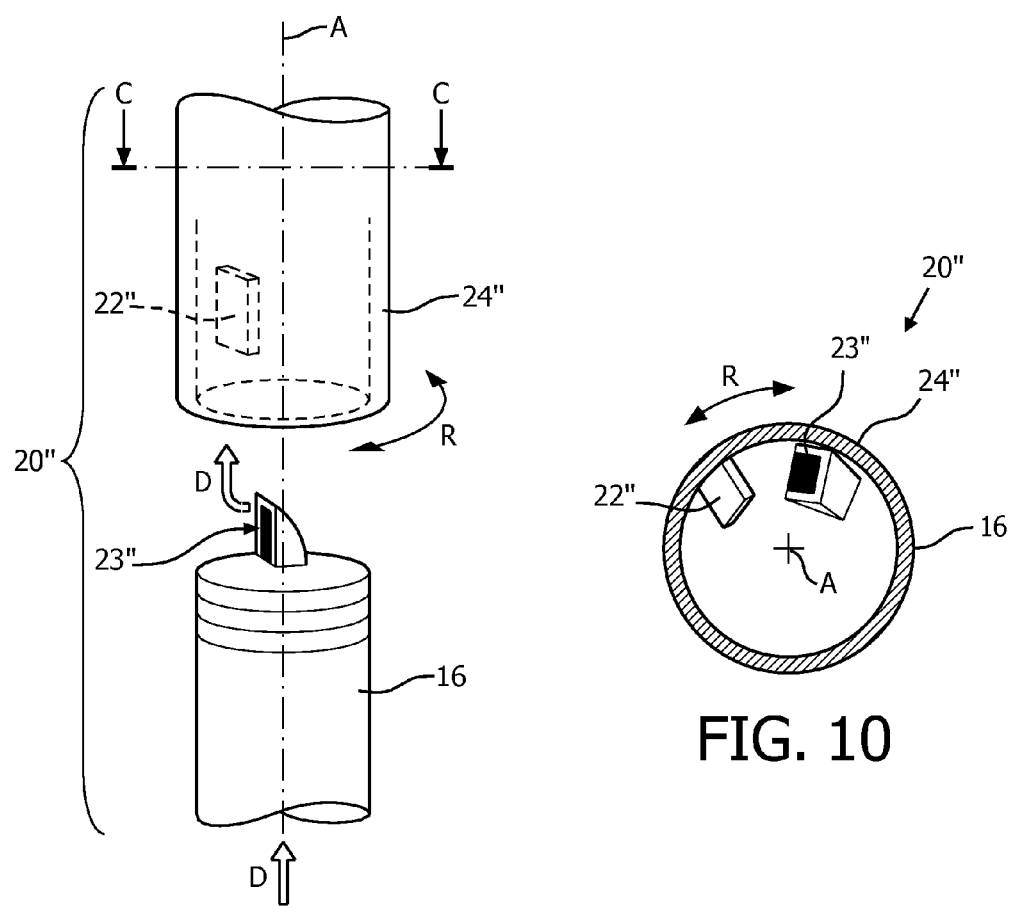

MANUALLY ACTUATED TALK VALVE FOR A RESPIRATORY DEVICE

CROSS-REFERENCE TO RELATED APPLICATIONS

This patent application claims the priority benefit under 35 U.S.C. §371 of international patent application no. PCT/IB2011/053627, filed Aug. 17, 2011, which claims the priority benefit under 35 U.S.C. §119(e) of U.S. Provisional Application No. 61/375,110 filed on Aug. 19, 2010, the contents of which are herein incorporated by reference.

BACKGROUND OF THE INVENTION

1. Field of the Invention

The present invention pertains to an interface system for use in providing a flow of pressurized gas to a patient, and, in particular, to an interface system having a manually actuated valve structured to selectively impede the flow of pressurized gas to the patient. The invention also relates to a conduit having such a valve and to a method of providing a flow of pressurized gas to a patient using such a valve.

2. Description of the Related Art

There are numerous situations where it is necessary or desirable to deliver a pressurized flow of breathing gas non-invasively to the airway of a patient, i.e., without intubating the patient or surgically inserting a tracheal tube in the esophagus. For example, it is known to ventilate a patient using a technique known as non-invasive ventilation. It is also known to deliver continuous positive airway pressure (CPAP) or variable airway pressure, such as a bi-level pressure that varies with the patient's respiratory cycle or an auto-titrating pressure that varies with the monitored condition of the patient. Typical pressure support therapies are provided to treat a medical disorder, such as sleep apnea syndrome, in particular, obstructive sleep apnea (OSA), or congestive heart failure.

During such treatments, a supply of pressurized gas is typically supplied to a patient through a patient interface, such as a nasal, oral, or combination nasal/oral mask. While wearing such an interface that is providing pressure, a patient commonly experiences difficulty speaking. Such difficulty generally occurs most dramatically in nasal masks, but is also a problem in full face mask applications, commonly used to treat obstructive sleep apnea. In such instances, as a person attempts to speak, they must fight the pressure and flow of the gas supply. This causes the patient's voice to become distorted, which is a major inconvenience to the user. If a person attempts to remove the mask as they speak, they risk changing or losing the seal as they re-apply the mask. Noise also generally increases in mask removal as the machine (typically CPAP) ramps up flow in an attempt to reach nominal pressure, without resistance. To stop the flow, and speak comfortably, the user must shut off the machine, which could be located an inconvenient distance away.

SUMMARY OF THE INVENTION

Accordingly, it is an object of the present invention to provide an interface system that overcomes the shortcomings of conventional patient interface systems. This object is achieved according to one embodiment of the present invention by providing an interface system for use in providing a flow of pressurized gas to a patient. The interface system comprises a patient interface structured to communicate a flow of gas to an airway of a patient. A conduit is coupled to the patient interface. The conduit is structured to communicate the flow of pressurized gas to the patient interface. A valve mechanism is disposed in or about the conduit. The valve mechanism is structured to selectively impede the flow of pressurized gas to the patient. The valve mechanism includes a manually manipulated element to enable a user actuate the valve mechanism so that the user can control the application of the flow of the gas to his or her airway. This is advantageous, for example, so that the user can substantially block the flow when he/she desires to speak, so that the user is not attempting to talk against a flow of gas.

According to another embodiment of the present invention, a conduit for use in providing a flow of pressurized gas to a patient is provided. The conduit comprises a housing having a first end and an opposite second end, the first end being structured to be coupled to a patient interface and the second end being structured to be coupled to a pressurized gas supply. The housing is structured to communicate the flow of pressurized gas therethrough. The conduit also comprises a valve mechanism coupled to the housing. The valve mechanism comprises a gate member selectively moveable between a first position in which the gate member is structured to generally not impede the flow of pressurized gas through the housing and a second position in which the gate member is structured to impede the flow of pressurized gas through the housing. The valve mechanism includes a manually manipulated element to enable a user actuate the valve mechanism so that the user can control the application of the flow of the gas to his or her airway.

According to a further embodiment of the present invention, a method of providing a supply of pressurized gas to a patient is provided. The method comprising providing an interface system structured to engage a nasal and/or oral orifice of the patient, providing a flow of gas to the interface system, and providing a valve mechanism in the flow of gas. The valve mechanism including a manually manipulated element to enable a user actuate the valve mechanism so that the user can selectively impede the flow of pressurized gas to the patient when activated by the patient.

These and other objects, features, and characteristics of the present invention, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention. As used in the specification and in the claims, the singular form of "a", "an", and "the" include plural referents unless the context clearly dictates otherwise.

BRIEF DESCRIPTION OF THE DRAWINGS

FIGS. 4-6 are schematic views of an example valve mechanism according to another non-limiting embodiment of the present invention;

FIG. 9 is a schematic exploded view of a further example valve mechanism according to a further non-limiting embodiment of the present invention; and FIG. 10 is a schematic view of the example valve mechanism of FIG. 9 along C-C.

DETAILED DESCRIPTION OF THE EXEMPLARY EMBODIMENTS

Figure 1:
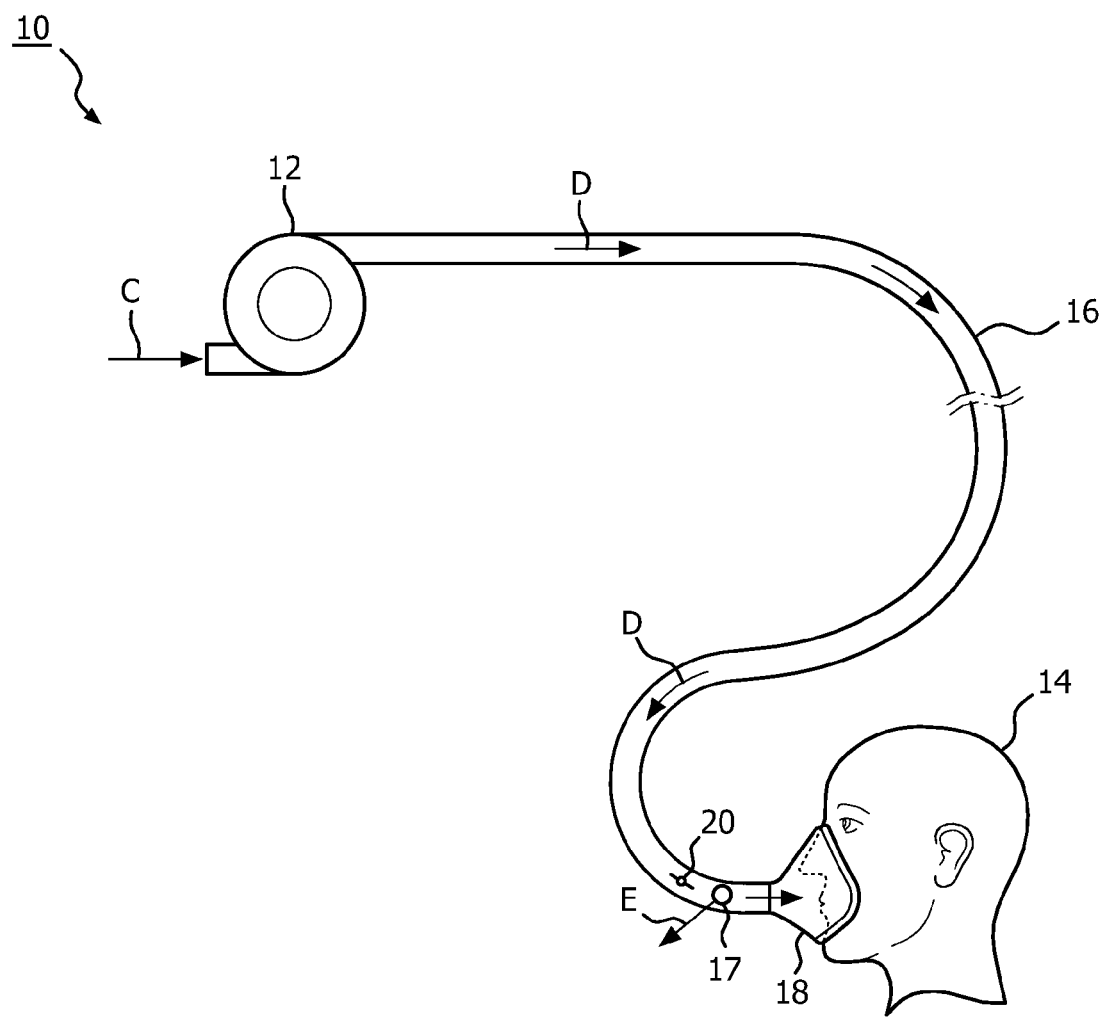
FIG. 1 is a schematic diagram of a pressure support system according to the principles of the present invention.

As used herein, the singular form of "a", "an", and "the" include plural references unless the context clearly dictates otherwise. As used herein, the statement that two or more parts or components are "coupled" shall mean that the parts are joined or operate together either directly or indirectly, i.e., through one or more intermediate parts or components, so long as a link occurs. As used herein, "directly coupled" means that two elements are directly in contact with each other. As used herein, "fixedly coupled" or "fixed" means that two components are coupled so as to move as one while maintaining a constant orientation relative to each other.

As used herein, the word "unitary" means a component is created as a single piece or unit. That is, a component that includes pieces that are created separately and then coupled together as a unit is not a "unitary" component or body. As employed herein, the statement that two or more parts or components "engage" one another shall mean that the parts exert a force against one another either directly or through one or more intermediate parts or components. As employed herein, the term "number" shall mean one or an integer greater than one (i.e., a plurality).

Directional phrases used herein, such as, for example and without limitation, top, bottom, left, right, upper, lower, front, back, and derivatives thereof, relate to the orientation of the elements shown in the drawings and are not limiting upon the claims unless expressly recited therein.

The present invention addresses shortcomings of the prior art by placing a valve in, adjacent to, or in general proximity thereof, the patient interface system, in the pressurized gas flow channel. The purpose of the valve is to momentarily stop, or significantly restrict, the flow of pressurized gas to the patient and allow for talking. If a patient wants to speak, they can simply actuate the valve, and speak with ease, while staying in the same comfortable position as before. Upon being released by the patient, the valve automatically returns to the unactivated state. This automatic return to the unactivated (open) state avoids the problem with the user forgetting to manually change the position of the valve. The valve has validity in home and hospital use, and additionally would be useful in trialing and fitting applications, where speaking could be necessary.

FIG. 1 is a schematic diagram of pressure support system 10 according to one particular, non-limiting embodiment in which the present invention in its various embodiments may be implemented. Referring to FIG. 1, pressure support system 10 includes a gas flow generator 12, such as a blower used in a conventional CPAP or bi-level pressure support device, which receives breathing gas, generally indicated by arrow C, from any suitable source, e.g., a pressurized tank of oxygen or air, the ambient atmosphere, or a combination thereof. Gas flow generator 12 generates a flow of breathing gas, such as air, oxygen, or a mixture thereof, for delivery to an airway of a patient 14 at relatively higher and lower pressures, i.e., generally equal to or above ambient atmospheric pressure. In the exemplary embodiment, gas flow generator 12 is capable of providing a flow of breathing gas generally ranging in pressure from 3-30 cmH$_2$O.

The pressurized flow of breathing gas, generally indicated by arrow D, from gas flow generator 12 is delivered via a delivery conduit 16 to a patient interface 18. Patient interface 18 can be of any known construction, such as a nasal mask, nasal/oral mask, nasal cannula, total face mask, tracheal tube, endotracheal tube, or any other device that is typically worn by, or otherwise attached to, patient 14 to communicate the flow of breathing gas to the airway of patient 14. Delivery conduit 16 is also typically referred to as a patient circuit. For present purposes, an interface system is defined as the combination of a patient interface and at least a portion of conduit 16.

Pressure support system 10 of FIG. 1 is what is known as a single-limb system, meaning that the patient circuit includes only a single delivery conduit 16 connecting patient 14 to pressure support system 10. As such, an exhaust vent 17 is provided in delivery conduit 16 for venting exhaled gasses from the system, as indicated by arrow E. It should be noted that exhaust vent 17 can be provided at other locations in addition to, or instead of, in delivery conduit 16, such as in patient interface 18. It should also be understood that exhaust vent 17 can have a wide variety of configurations depending on the desired manner in which gas is to be vented from pressure support system 10.

Continuing to refer to FIG. 1, pressure support system 10 further includes a talk valve mechanism 20 disposed along delivery conduit 16. As will be discussed in greater detail below, valve mechanism 20 is provided to allow a patient to selectively temporarily stop, or substantially stop, the pressurized flow of gas being delivered to the patient. This complete or partial cessation of the flow of gas to the airway of the patient allows the patient to speak without interference from the pressurized gas flow. It should be noted, as will also be discussed further below, that valve mechanism 20 can be provided at other locations in addition to, or instead of, in delivery conduit 16, such as in patient interface 18 adjacent delivery conduit 16. However, it is generally desirable that valve mechanism 20 be located at a position that is readily and comfortably accessed by a patient.

Figure 2:
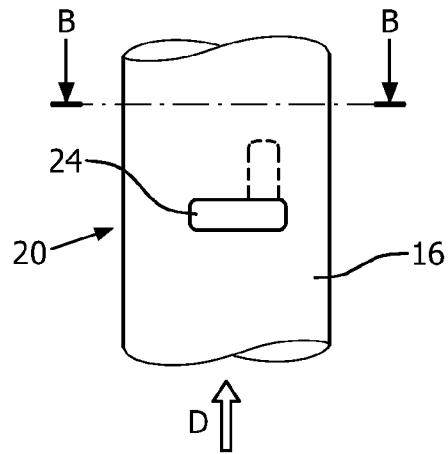
FIG. 2 is a schematic side view of an example valve mechanism according to a non-limiting embodiment of the present invention.
Figure 3A:
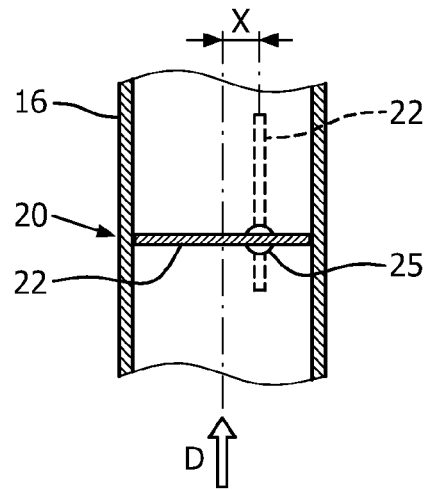
FIG. 3A is a schematic cross-sectional view of the example valve mechanism of FIG. 2.
Figure 3B:
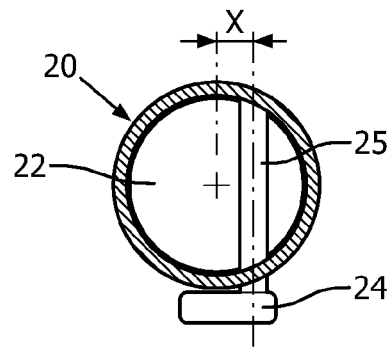
FIG. 3B is a schematic cross sectional end view of the example valve mechanism of FIG. 2 along B-B.

As shown in the example embodiment of FIGS. 2, 3A, and 3B, valve mechanism 20 may be constructed similar to a butterfly valve, such that a rotating plate or gate member 22 is disposed within delivery conduit 16. As shown in FIG. 3B, gate member 22 is of similar size and shape as the internal cross-section (not numbered) of conduit 16 such that when positioned as shown in solid line in FIGS. 3A and 3B, gas flow D is completely, or at least substantially, stopped. Gate member 22 is moveable among a first position (shown in dashed line in the cross-sectional view of FIG. 3A) in which gate member 22 generally does not impede the flow D of gas within conduit 16, and a second position (shown in solid line in the cross-sectional view of FIG. 3A) in which gate member 22 has been rotated with respect to conduit 16 and thus impedes or substantially impedes the flow D of gas within conduit 16.

In an exemplary embodiment, movement of gate member 22 is selectable by a patient through actuation of a manually manipulated element, such as a rotatable switch mechanism 24 (FIG. 2). Such switch mechanisms, include, but are not limited to, a knob or lever, that is generally disposed external to conduit 16 and coupled to gate member 22 by way of a rotatable shaft 25. It is to be appreciated that gate member 22 is thus rotatably coupled to conduit 16 by way of shaft 25, which, as shown in FIGS. 3A and 3B, is preferably offset a distance x from the centerline of conduit 16. Such offset generally provides for gate member 22 to be biased in the first (open) position by the flow D of gas within conduit 16 when switch mechanism 24 is not being activated upon by a patient. It is further to be appreciated that a spring member (not shown) or other suitable mechanism may be provided to bias gate member 22 generally in the first (open) position such that the flow D of gas within conduit 16 is not interrupted unless switch mechanism 24 is being activated by a patient.

FIGS. 4-6 show another example embodiment of a valve mechanism 20' that may be disposed adjacent delivery conduit 16. As shown in the cross-sectional views of FIGS. 5 and 6, valve mechanism 20' employs a generally hemispherical gate member 22' that interacts with a reduced diameter portion 23' to stop or substantially stop gas flow D. FIG. 5 shows the valve mechanism 20' in a first (open) position wherein gate member 22' is spaced apart from reduced diameter portion 23', thus allowing gas flow D to pass therethrough. It is to be appreciated that the pressure of flow D is generally sufficient to keep gate member 22' biased in such first position. However, a spring mechanism (not shown) may also be employed, either internal or external to conduit 16, to bias gate member 22' in the first (open) position.

FIG. 6 shows the valve mechanism 20' displaced axially with respect to conduit 16 in a second (closed) position wherein gate member 22' is generally in contact with reduced diameter portion 23', thus obstructing, or substantially obstructing, gas flow D. Such displacement of gate member 22' from the first position (FIG. 5) to the second position (FIG. 6) may readily be accomplished by a patient pushing downward on switch mechanism 24', which is formed as a collar generally surrounding an outer portion of conduit 16. As shown in the example embodiment of FIGS. 4-6, an additional non-moveable fixed collar 25' may be rigidly coupled to, or integrally formed with, conduit 16 in order to provide a positive stop, and also to avoid possible damage to valve mechanism 20' due to over-actuation.

Figure 7:
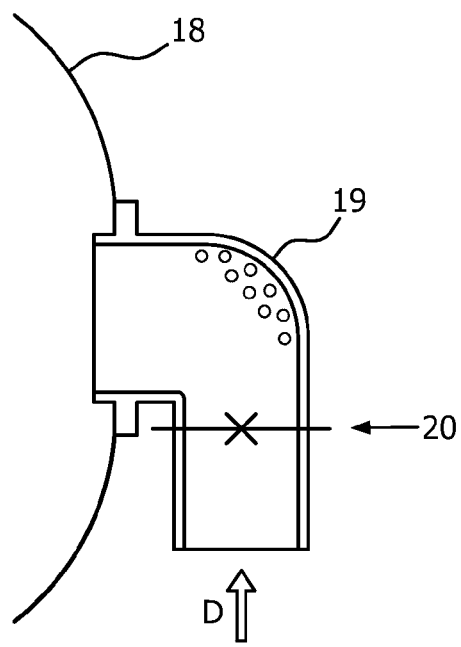
FIGS. 7 and 8 are schematic views of further example valve mechanisms according to non-limiting embodiments of the present invention.
Figure 8:
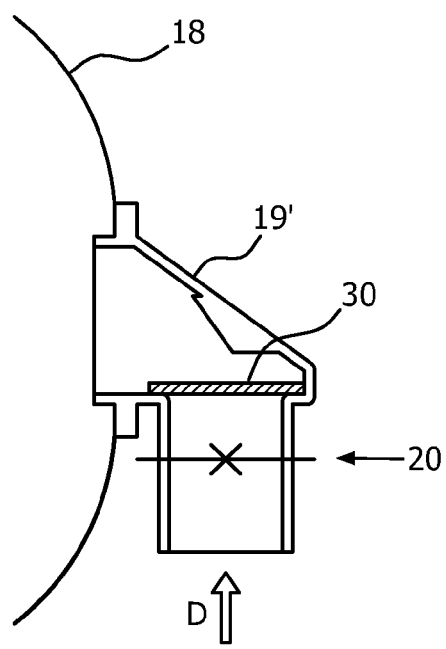

FIGS. 7 and 8 show cross-sectional views of example embodiments of the present invention in which a valve, such as valve mechanism 20 previously discussed, has been placed in an elbow 19, 19' adjacent a patient interface 18. FIG. 8 shows such placement of valve mechanism 20 before an entrainment valve 30.

FIGS. 9 and 10 show a further example embodiment of a valve mechanism 20" that may be disposed adjacent delivery conduit 16. Valve mechanism 20" employs a gate member 22" that extends generally inward from a switch mechanism 24" that is generally rotatable about a central axis A, as shown by arrow R. Gate member 22" interacts with a reduced diameter portion 23" to stop or substantially stop gas flow D. It is to be appreciated that the pressure of flow D is generally sufficient to keep gate member 22" biased in an open (first) position. However, a spring mechansim (not shown) may also be employed, either internal or external to conduit 16, to bias gate member 22" in the first (open) position. When a patient wishes to activate valve mechanism 20", the patient simply twists switch mechanism 24" relative to conduit 16, thus causing gate member 22" to engage reduced diameter portion 23", thus stopping, or at least substantially stopping gas flow D.

It is to be appreciated that other suitable valve mechanisms other than those examples described herein may be employed without varying from the scope of the present invention. For example, the movement/position of the gating element can be controlled via an electronic motor rather than the mechanical structures shown in the figures and described above. In addition to blocking the flow of gas (either completely or partially), the present invention contemplates diverting the flow from the patient circuit to the ambient atmosphere in addition to or in place of blocking the flow, either totally or partially.

It is to be further appreciated that the elbows described herein may instead of being formed as a separate piece, may be incorporated into, and thus formed as a part of, a patient interface system. The present invention further contemplates that the valve mechanism may be formed within patient interface 18, rather than be provided in or along the gas delivery conduit. For example, a manually actuated iris or shutter valve can be provided at the opening in the patient interface to which conduit 16 or elbow 19 is connected.

It can be still further appreciated that the present invention provides a patient interface employing a mechanism that assists a patient desiring to speak while minimizing interference with the treatment.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims. For example, it is to be understood that the present invention contemplates that, to the extent possible, one or more features of any embodiment can be combined with one or more features of any other embodiment.

What is claimed is:

1. An interface system for use in providing a flow of pressurized gas to a patient, the interface system comprising:
   a patient interface structured to engage a nasal and/or oral orifice of a patient;
   a conduit coupled to the patient interface, the conduit being disposed generally about a central axis and being structured to communicate the flow of pressurized gas to the patient interface; and
   a valve mechanism operatively coupled to the patient interface or the conduit, the valve mechanism being structured to selectively impede the flow of pressurized gas to an airway of such a patient, wherein the valve mechanism includes a manually manipulated element to enable the patient to actuate the valve mechanism, wherein the valve mechanism comprises a gate member selectively moveable between a first position in which the gate member is structured to generally not impede the flow of pressurized gas to the patient and a second position in which the gate member is structured to impede the flow of pressurized gas to the patient, and wherein the gate member is biased toward the first position,
   wherein the manually manipulated element comprises a switch portion adapted to move the gate member between the first position and the second position upon engagement of the switch portion by the patient, and
   wherein the switch portion is:
   (a) rotatable about another axis oriented generally perpendicular to the central axis,
   (b) generally slidable in a direction parallel to the central axis, or
   (c) rotatable about the central axis.

2. The interface system of claim 1, wherein the gate member comprises a spring member disposed in a manner that biases the gate member in the first position.

3. The interface system of claim 1, wherein the switch portion comprises:

(a) a lever disposed on an external portion of the mask or the conduit, or (b) a collar member disposed on, and generally surrounding, an external portion of the conduit.

4. A conduit for use in providing a flow of pressurized gas to a patient, the conduit comprising:

(a) a housing having a first end and an opposite second end, the first end being structured to be coupled to a patient interface and the second end being structured to be coupled to a pressurized gas supply, the housing being structured to communicate the flow of pressurized gas therethrough; and (b) a valve mechanism coupled to the housing, the valve mechanism comprising:

(1) a gate member selectively moveable between a first position in which the gate member is structured to generally not impede the flow of pressurized gas through the housing and a second position in which the gate member is structured to impede the flow of pressurized gas through the housing, and (2) a manually manipulated element to enable the patient to actuate the valve mechanism, wherein the gate member is biased toward the first position, wherein the manually manipulated element comprises a switch portion being adapted to move the gate member between the first and the second position upon engagement by the patient, and wherein the switch portion comprises a lever disposed on an external portion of the housing, or a collar member disposed on, and generally surrounding, an external portion of the housing.

5. The conduit of claim 4, wherein the gate member is structured to be biased in the first position by the flow of pressurized gas.

6. The conduit of claim 4, wherein the gate member comprises a spring member disposed in a manner that biases the gate member in the first position.

* * * * *